US012745941B2

(12) United States Patent
Vrijens et al.

(10) Patent No.: US 12,745,941 B2
(45) Date of Patent: Sep. 29, 2026

(54) SOFT AND DRY ELECTRODE

(71) Applicant: Dätwyler Schweiz AG, Schattdorf (CH)

(72) Inventors: Ronny Vrijens, Vliermaalroot (BE); Mattia Alberto Lucchini, Lucerne (CH); Raphael Kaelin, Hergiswil (CH); Michael Segessenmann, Bürglen (CH)

(73) Assignee: Dätwyler Schweiz AG, Schattdorf (CH)

( * ) Notice: Subject to any disclaimer, the term of this patent is extended or adjusted under 35 U.S.C. 154(b) by 469 days.

(21) Appl. No.: 18/024,305

(22) PCT Filed: Aug. 19, 2021

(86) PCT No.: PCT/CH2021/050019

§ 371 (c)(1),
(2) Date: Mar. 2, 2023

(87) PCT Pub. No.: WO2022/047595

PCT Pub. Date: Mar. 10, 2022

(65) Prior Publication Data

US 2023/0263447 A1 Aug. 24, 2023

(30) Foreign Application Priority Data

Sep. 3, 2020 (CH) .................................... 01087/20

(51) Int. Cl.
*A61B 5/268* (2021.01)
*A61B 5/273* (2021.01)
*H01B 1/12* (2006.01)

(52) U.S. Cl.
CPC .............. *A61B 5/268* (2021.01); *A61B 5/273* (2021.01); *H01B 1/124* (2013.01)

(58) Field of Classification Search
CPC .......... A61B 5/268; A61B 5/273; H01B 1/124
See application file for complete search history.

(56) References Cited

U.S. PATENT DOCUMENTS 8,731,633 B2 * 5/2014 Asjes ..................... A61B 5/369 600/383
2015/0238100 A1 * 8/2015 Lin .......................... A61B 5/25 600/393

(Continued)

FOREIGN PATENT DOCUMENTS

EP 2827770 B1 5/2018
JP 2017074370 A 4/2017

(Continued)

OTHER PUBLICATIONS

Kumagai N, Translation of JP 2019097733, 2019 (Year: 2019).*

(Continued)

*Primary Examiner* — Adam Z Minchella
(74) *Attorney, Agent, or Firm* — Fleit Intellectual Property Law; Paul D. Bianco; Kaela A. Stephano

(57) ABSTRACT

An electrode for measuring bioelectric signals of an individual includes a dome-like shape support body having a concave contact side facing the individual and an opposite convex connector side. The support body defines a central axis arranged centrally through the contact and connector sides. The electrode includes outer contact pins located on the contact side at a radially outer region of the support body for contacting an area of interest to be measured. The electrode is made of elastomeric material and has conductive properties. The support body is flexible such that after applying the electrode to the individual a force exerted centrally onto the connector side and parallel to the central axis leads to an upwards bending of the radially outer region. The upwards bending leads to tilting of the outer contact pins such that a tip of the outer contact pins moves radially outwards along the area of interest.

11 Claims, 2 Drawing Sheets

(56) References Cited

U.S. PATENT DOCUMENTS

| | | | | |
|---|---|---|---|---|
| 2016/0143554 | A1* | 5/2016 | Lim | A61B 5/291 600/386 |
| 2016/0174859 | A1* | 6/2016 | Oudenhoven | A61B 5/053 600/383 |
| 2020/0029881 | A1* | 1/2020 | Flood | A61B 5/375 |
| 2021/0393185 | A1 | 12/2021 | Kitazoe | |

FOREIGN PATENT DOCUMENTS

| | | | |
|---|---|---|---|
| JP | 2018175288 | A | 11/2018 |
| JP | 2019097733 | A * | 6/2019 |
| WO | 2016/080804 | A1 | 5/2016 |
| WO | 2020095589 | A1 | 5/2020 |

OTHER PUBLICATIONS

International Search Report and Written Opinion for PCT/CH2021/050019, filed Aug. 19, 2021.
International Preliminary Report on Patentability and Written Opinion for PCT/CH2021/050019, filed Aug. 19, 2021.
Japanese Office Action dated Jun. 27, 2025 for Japanese Patent Application No. 2023-515058.

* cited by examiner

FIG. 1A
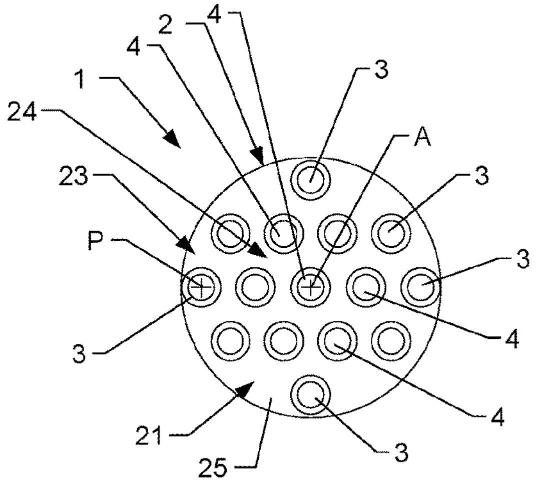
FIG. 1B
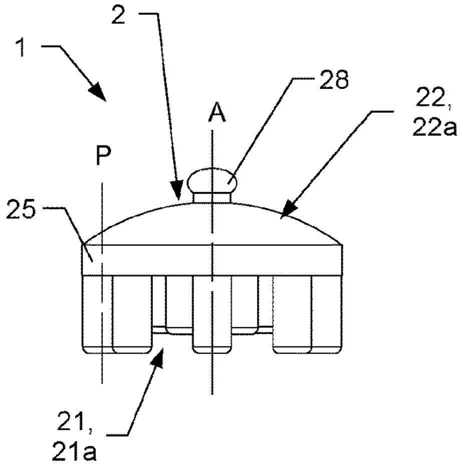
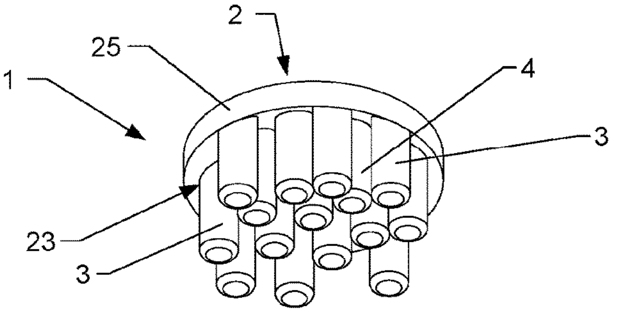
FIG. 1C
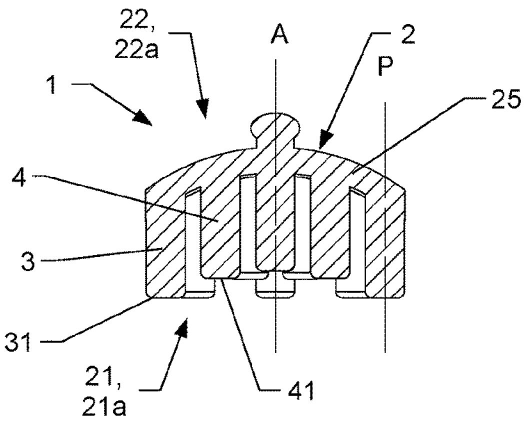
FIG. 2A
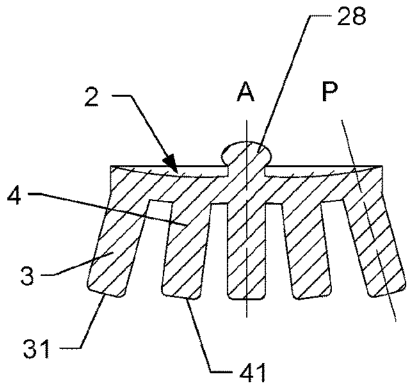
FIG. 2B FIG. 3A
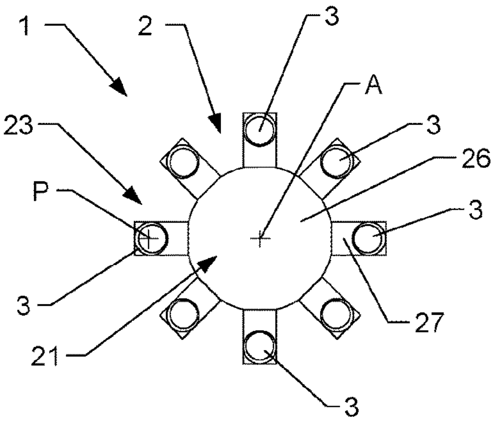
FIG. 3B
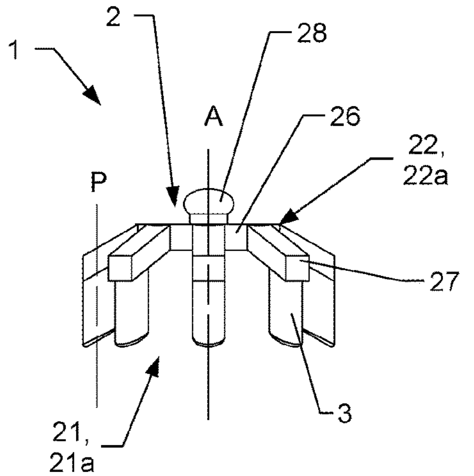
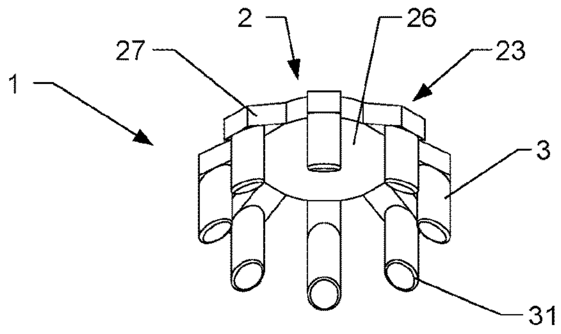
FIG. 3C
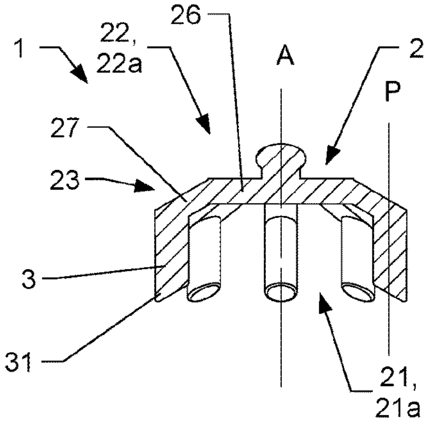
FIG. 4A
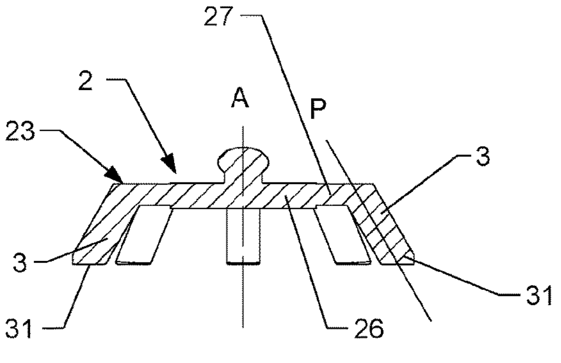
FIG. 4B

SOFT AND DRY ELECTRODE

TECHNICAL FIELD

The invention relates to soft and dry electrodes for detection of bioelectric signals in applications such as electroencephalography (EEG), electrocardiography (ECG) or electromyography (EMG).

BACKGROUND

Commercially available 'dry' EEG headsets are often equipped with metal dry electrodes, which causes subjects to feel pain after wearing the headsets for a while. A possible solution is combining such electrodes with a spring-like system to avoid high skin pressure.

Yet another approach is the use of soft polymer-based dry electrodes. By mixing the elastic polymer with additives the conductivity can be improved while maintaining the required elasticity for high user comfort. The polymer based dry electrodes can have a comb shape design (fingers or legs) to improve skin contact on hairy skin (e.g. on the scalp). Such fingers or legs can have at least a partial coating on a surface of the electrode in contact with the skin in order to lower the skin impedance and provide an improved signal quality.

Thus, soft and dry electrodes are increasingly used for long term biopotential measurements such as EEG and ECG. Next to being soft, the additional fact that such electrodes can be applied without the use of a conductive gel provides the measurement procedure with considerable benefits such as a decreased risk of skin irritation and the avoidance of a decrease of signal quality due to gel drying.

Examples of such soft and dry electrodes are described by Chen et al. in "Polymer-based dry electrodes for high user comfort ECG/EEG measurements" (Chen, Yun-Hsuan; Op de Beeck, Maaike; Carrette, Evelien; Vanderheyden, Luc; Grundlehner, Bernard; Mihajlovic, Vojkan; Boon, Paul; Van Hoof, Chris; Apprimus Verlag; Aachen; 8th International Conference Exhibition on Integration Issues of Miniaturized Systems—MEMS, NEMS, ICs and Electronic Components; 2014; pp. 329-336), Chen et al. in "Soft, Comfortable Polymer Dry Electrodes for High Quality ECG and EEG Recording" (Sensors 2014, 14, 23758-23780; doi:10.3390/s141223758) or WO2016080804.

These soft and dry electrodes comprise a base plate and a plurality of pins for contacting an area of interest to be measured. The pins may have a tapered portion and a protruding portion. The electrode tips are made of a flexible or soft matrix material which is provided with an electrically conductive material. The electrodes may have a knob on its upper side of the base plate opposite of the pins for electrically connecting the electrode.

Upon exertion of force on the soft electrode (e.g. by means of a strap, band, headset or head-cap) the legs may move in an uncontrolled manner, not offering the intended brush function to move aside hair and provide for a direct contact between electrode and skin surface.

One possible solution for this problem is a pre-orientation of the legs (as described in EP2827770) so that on applying the electrode to the subject area (e.g. a scalp) these legs are disposed at a non-perpendicular angle to that subject area. A downside of this approach however is the adopted manufacturing process involving a 3D-printing step which is not suitable for up-scaling towards high volume productions.

JP20190977332 relates to an electrode for measuring brain activity. The electrode has a stiff support body and several arms attached at the side of the stiff support body. A ball is formed at the tip of the arms to contact the scalp of a person. The arms are flexible and bend when a force is applied to the electrode. The electrode has a complex shape with several undercuts, which makes it difficult to manufacture in a cost-efficient way.

SUMMARY OF THE INVENTION

One aspect of the invention relates to a soft electrode for measuring bioelectric signals of an individual avoiding the problems of the prior art and being suitable for high volume production.

Accordingly, a soft electrode for measuring bioelectric signals of an individual is disclosed herein. The soft electrode comprises a support body having a contact side facing the individual when applying the electrode to the individual and a connector side opposite the contact side. The connector side serves for connecting the electrode to an electronic circuit. The support body defines a central axis arranged centrally through the contact side and the connector side. The electrode further comprises a plurality of outer pins located at a radially outer region of the support body for contacting an area of interest to be measured. The plurality of outer pins being supported and arranged on the contact side of the support body. The electrode is made of elastomeric material and has electrically conductive properties. The support body has a dome-like shape having a concave side and a convex side, wherein the concave side forms the contact side of the support body. The support body is designed with a flexibility such that after applying the electrode to the individual a force exerted centrally onto the connector side and parallel to the central axis leads to an upwards bending of the radially outer region of the support body in direction of the connector side. The upwards bending of the radially outer region of the support body leads to a tilting of the plurality of outer contact pins relative to the central axis such that a tip of the outer contact pins moves radially outwards along the area of interest of the individual.

In other words, upon force exertion on the top surface of the support body, the flexible support body starts bending such that the tip of the pins or legs move in an outward direction (i.e. away from the centre of the electrode) in order to 'brush aside' any hair that is hindering direct contact between electrode and bare skin surface of the individual to be measured. Additionally, the use of elastomeric materials, e.g. a thermoset elastomer or a thermoplastic elastomer (TPE) and the dome-like shape of the support body with a plurality of pins parallel to the central axis of the support body allow for production methods such as injection moulding, compressing moulding, injection transfer moulding, injection compression moulding, etc. These type of production methods allow high volume production of the electrodes.

Further embodiments of the invention are also disclosed herein.

In some embodiments a longitudinal axis of each of the plurality of outer pins is parallel to the central axis.

In some embodiments, the electrode may further comprise a plurality of inner contact pins located at an inner region of the support body closer to the central axis than the outer region of the support body and being dimensioned to contact the individual after the tilting of the outer contact pins occurred.

In some embodiments, the plurality of outer contact pins and the plurality of inner contact pins may have the same length. Alternatively, the plurality of outer contact pins and the plurality of inner contact pins may have different length, preferably the inner contact pins have a shorter length than the outer contact pins. For instance, the pins positioned in a more central region of the electrode can have a shorter length so that they will only start touching the skin surface (e.g. scalp) when the outer pins have been tilting outwards and moving aside hair in order to prepare a bare skin for these central pins to touch.

In some embodiments, the plurality of outer contact pins and the plurality of inner contact pins may be arranged and dimensioned such that while applying the electrode to the individual the plurality of outer contact pins contact the area of interest before the plurality of inner contact pins.

In some embodiments, the plurality of outer contact pins and/or the plurality of inner contact pins may comprise a cone-shaped base portion and a cylinder-shaped free end portion. The free end portion forms the tip of the pin.

In some embodiments, the support body may be a dome-shaped disc, preferably a circular disc. The disc in the sense of the invention may have a quasi-circular shape such as oval, or polygonal, e.g. triangular, penta- or hexagonal or the like.

In some embodiments, the support body may comprise a central disc, preferably a circular disc with a plurality of legs directed radially outwards, at an angle to the central axis of less than 90 degrees, preferably 30 to 70 degrees, and defining the outer region of the dome-shaped support body, wherein the plurality of outer contact pins are arranged at the free end of the legs.

In some embodiments, the connector side of the support body may be provided with a knob or a so-called male snap fit for electrically connecting the electrode to an electronic circuit. The knob or male snap fit may be of the same soft electrically conductive material as the electrode or in a rigid material (e.g. metal, plastic) for facilitating the connection with an electronic circuit.

In some embodiments, the tip of the plurality of outer contact pins may comprise an inclined surface facing towards the central axis of the support body.

In some embodiments the connector side of the support body may be provided with slits or grooves surrounding a base portion of the contact pins to increase flexibility of the support body.

In some embodiments, the elastomeric material of the electrode may be a thermoset elastomer or a thermoplastic elastomer.

The elastomeric material can be, for example, a synthetic or natural rubber, such as butyl rubber, isoprene rubber, butadiene rubber, halogenated butyl rubber (e.g., bromobutyl rubber), ethylene propylene terpolymer, silicone rubber, fluoro- or perfluoroelastomers, chlorosulfonate, polybutadiene, butyl, neoprene, nitrile, polyisoprene, buna-N, copolymer rubbers such as ethylene-propylene (EPR), ethylene-propylene-diene monomer (EPDM), acrylonitrile-butadiene (NBR or HNBR) and styrene-butadiene (SBR), blends such as ethylene or propylene-EPDM, EPR, or NBR, combinations thereof. The term "synthetic rubbers" also should be understood to encompass materials which alternatively may be classified broadly as thermoplastic or thermosetting elastomers such as polyurethanes, silicones, fluorosilicones, styrene-isoprene-styrene (SIS), and styrene-butadiene-styrene (SBS), as well as other polymers which exhibit rubber-like properties such as plasticized nylons, polyolefins, polyesters, ethylene vinyl acetates, fluoropolymers, and polyvinyl chloride.

Good results may be achieved with ethylene propylene diene mono rubber (EPDM), silicone rubber (SR), liquid silicone rubber (LSR), butyl rubber, isoprene or nitrile rubber.

In some embodiments, the conductive properties of the electrode may be achieved by adding conductive material to the elastomeric material. The conductive material may be carbon black, silver coated glass spheres, silver particles, Ag-coated aluminium beads, Ag-coated glass fibres, graphene, carbon nanotubes, graphite, stainless steel fibres, or any other suitable material. Conductive properties of the electrode may also be achieved by coating the electrode with conductive material, e.g. Ag—AgCl or PEDOT:PSS.

In some embodiments, the coating may also be applied in addition to the conductive elastomeric material. Such additional coating may be applied on the tips of the pins only.

In some embodiments, the electrode may be formed as a single piece.

BRIEF DESCRIPTION OF THE DRAWINGS

The invention is described in greater detail below with reference to embodiments that are illustrated in the figures. The figures show:

FIGS. 1A-1C a bottom view (FIG. 1A), a side view (FIG. 1B) and a perspective view (FIG. 1C) of an electrode with a dome-shaped circular disk;

FIGS. 2A-2B sectional views of the electrode of FIGS. 1A-1C before (FIG. 2A) and after (FIG. 2B) exerting a force to the electrode;

FIGS. 3A-3C a bottom view (FIG. 3A), a side view (FIG. 3B) and a perspective view (FIG. 3C) of an electrode with a dome-like support body with legs; and FIGS. 4A and 4B sectional views of the electrode of FIGS. 3A-3C before (FIG. 4A) and after (FIG. 4B) exerting a force to the electrode.

EMBODIMENTS OF THE INVENTION

FIGS. 1A-1C a bottom view (FIG. 1A), a side view (FIG. 1B) and a perspective view (FIG. 1C) of a soft and dry electrode 1 for measuring bioelectric signals of an individual. FIGS. 2A and 2B show sectional views of the electrode of FIGS. 1A-1C before (FIG. 2A) and after (FIG. 2B) exerting a force to the electrode.

The electrode 1 is made of elastomeric material, which is provided with conductive additives and/or is at least partially coated with a conductive coating. The electrode 1 is formed as a single piece and comprises a dome-shaped support body 2, several outer contact pins 3 and several inner contact pins 4. The support body 2 forms a concave contact side 21 supporting the contact pins 3, 4 for contacting the individual and a convex connector side 22 opposite the contact side 21. The connector side 22 is provided with a connector knob 28 for electrically connecting the electrode 1 to an electronic circuit. The support body 2 defines a central axis A arranged centrally through the contact side 21 and the connector side 22.

The support body 2 supports the plurality of outer pins 3, which are arranged at a radially outer circumferential region 23 of the support body 2. A central axis P of each pin 3 is parallel to the central axis A of the support body. In other words, when applying the electrode to the individual, the pins 3 touch the contact area of the individual in a perpendicular direction.

The dome-shaped support body 2 is flexible such that the radially outer region 23 of the support body 2 may bend upwards (i.e. away from the individual) when a force is applied centrally onto the connector side 22 of the electrode 1 and parallel to the central axis A of the support body 2. Thus, while exerting force onto the connector side 22 of the electrode 1, each outer pin 3 starts to tilt and a tip 31 of each outer pin 3 slides in a radially outward direction along the skin of the individual and thereby brushes through hair that may be present. The contact of the electrode to the individual is thereby increased. To increase rigidity of each outer pin 3, it may comprise a cone-shaped base portion and a cylinder-shaped tip portion.

The electrode shown in FIGS. 1A-1C and FIGS. 2A and 2B additionally comprises inner pins 4. The outer and inner pins 3, 4 have the same length such that a tip 41 of the inner pins 4 is offset along the central axis A in direction of the connector side 22. Thus, while applying the electrode 1 to the individual, the outer pins 3 contact the contact area of the individual first.

To facilitate the sliding movement on the skin, the free end of the pins may be rounded or provided with an inclined surface facing towards the central axis of the support body.

FIGS. 3A-3C show a bottom view (FIG. 3A), a side view (FIG. 3B) and a perspective view (FIG. 3C) of a further embodiment of a soft and dry electrode 1 for measuring bioelectric signals of an individual. FIGS. 4A and 4B show sectional views of the electrode of FIGS. 3A-3C before (FIG. 4A) and after (FIG. 4B) exerting a force to the electrode.

In contrast to the electrode 1 of FIGS. 1A-1C the support body 2 of the electrode 1 of FIGS. 3A-3C comprises a central circular disc 26 and a plurality of legs 27. The legs 27 are evenly and circumferentially arranged and directed radially outwards at an angle to the central axis A of less than 90 degrees, preferably 30 to 70 degrees. The legs 27 define the outer region 23 of the dome-shaped support body 2. The plurality of outer contact pins 3 are arranged at the free end of the legs 27. In the embodiment shown, inner pins are not present. Alternatively, inner pins, which touch the individual only after the legs start bending may be present.

While exerting a force to the electrode 1, the outer tips of the legs 27 forming the outer region 23 of the support body 2 move upwards in direction of the connector side 23, i.e. approximately parallel to the central axis A. Thereby, the outer pins 3 tilt and the tip 31 of each outer pin 3 moves outwards, radially away from the central axis A and slides along the skin of the individual.

REFERENCE SIGNS

1 electrode
2 support body
21 contact side of support body
21*a* concave side
22 connector side of support body
22*a* convex side
23 outer region of support body
24 inner region of support body
25 dome-shaped circular disc
26 central circular disc
27 leg
28 knob
3 outer contact pin
31 tip of outer contact pin
4 inner contact pin
41 tip of inner contact pin
A central axis
P pin axis

The invention claimed is:

1. A soft electrode for measuring bioelectric signals of an individual, the electrode comprising:

a support body having a contact side facing the individual when applying the electrode to the individual and a connector side opposite the contact side, and the support body further defining a central axis arranged centrally through the contact side and the connector side;

the electrode further comprising a plurality of outer contact pins located at an outer region of the support body for contacting an area of interest to be measured, the plurality of outer contact pins being supported and arranged on the contact side of the support body;

wherein the electrode is made of elastomeric material and has conductive properties;

wherein the support body is a dome-shaped body having a concave side and a convex side, wherein the concave side forms the contact side of the support body, wherein the plurality of outer pins are attached at and extend from the concave contact side of the dome with each of the plurality of outer pins having an outer edge that that is parallel to the central axis of the support body, wherein the support body is designed with a flexibility such that after applying the electrode to the individual a force exerted centrally onto the connector side and parallel to the central axis leads to an upwards bending of the outer region of the dome-shaped disc in a direction of the connector side, wherein the upwards bending of the outer region of the dome-shaped disc leads to a tilting of the plurality of outer contact pins relative to the central axis such that a tip of the outer contact pins moves radially outwards along the area of interest of the individual.

2. The soft electrode according to claim 1, wherein a longitudinal axis of each of the plurality of outer contact pins is parallel to the central axis.

3. The soft electrode according to claim 1, wherein the electrode further comprises a plurality of inner contact pins located at an inner region of the support body closer to the central axis than the outer region of the support body and being dimensioned to contact the individual after the tilting of the outer contact pins occurred.

4. The soft electrode according to claim 3, wherein the plurality of outer contact pins and the plurality of inner contact pins have the same length.

5. The soft electrode according to claim 4, wherein the plurality of outer contact pins and the plurality of inner contact pins are arranged and dimensioned such that while applying the electrode to the individual the plurality of outer contact pins contact the area of interest before the plurality of inner contact pins.

6. The soft electrode according to claim 3, wherein the plurality of outer contact pins and/or the plurality of inner contact pins comprise a cone-shaped base portion and a cylinder-shaped free end portion.

7. The soft electrode according to claim 1, wherein the plurality of outer contact pins comprise a cone-shaped base portion and a cylinder-shaped free end portion.

8. The soft electrode according to claim 1, wherein the connector side of the support body is provided with a knob for electrically connecting the electrode to an electronic circuit.

9. The soft electrode according to claim 1, wherein the tip of the plurality of outer contact pins comprises an inclined surface facing towards the central axis of the support body.

10. The soft electrode according to claim 1, wherein the elastomeric material of the electrode is a thermoset elastomer or a thermoplastic elastomer.

11. The soft electrode according to claim 1, wherein the electrode is formed as a single piece.

* * * * *